United States Patent
Letarte et al.

(12) 
(10) Patent No.: US 6,463,814 B1
(45) Date of Patent: Oct. 15, 2002

(54) BIOAEROSOL SLIT IMPACTION SAMPLING DEVICE

(75) Inventors: Robert T. Letarte, Howell; Paul L. Lagraff, Brighton, both of MI (US)

(73) Assignee: Graftech, Brighton, MI (US)

( * ) Notice: Subject to any disclaimer, the term of this patent is extended or adjusted under 35 U.S.C. 154(b) by 11 days.

(21) Appl. No.: 09/705,602

(22) Filed: Nov. 3, 2000

Related U.S. Application Data

(60) Provisional application No. 60/163,872, filed on Nov. 5, 1999.

(51) Int. Cl.[7] .................................................. G01N 1/22
(52) U.S. Cl. ..................................................... 73/863.22
(58) Field of Search ........................... 73/863.22, 28.05, 73/28.06; 96/413

(56) References Cited

U.S. PATENT DOCUMENTS

| | | | | |
|---|---|---|---|---|
| 2,839,155 A | * | 6/1958 | Martin | 96/413 |
| 3,518,815 A | * | 7/1970 | McFarland et al. | 96/413 |
| 4,725,294 A | * | 2/1988 | Berger | 73/863.22 |
| 4,764,186 A | * | 8/1988 | Langer | 96/413 |
| 4,796,475 A | * | 1/1989 | Marpel | 73/863.22 |
| 4,926,679 A | * | 5/1990 | Dewhurst | 73/863.22 |
| 5,201,231 A | * | 4/1993 | Smith | 73/863.22 |
| 5,693,895 A | | 12/1997 | Baxter | |

* cited by examiner

*Primary Examiner*—Robert Raevis
(74) *Attorney, Agent, or Firm*—Artz & Artz, P.C.

(57) ABSTRACT

A slit impaction sampling device is for collecting airborne contaminants for subsequent analysis, includes a base with a microscope slide disposed thereon. The microscopic slide has an adhesive media located thereon to assist in adhering airborne particles on the microscopic slide. The base has a top cap secured thereto. The top cap has an inlet opening formed therethrough. The inlet opening has an outer venturi section and an inner laminar section that directs the air flow through the inlet opening into contact with the adhesive media such that the airborne particles form an impaction trace thereon. The air then flows around the microscope slide into an outlet passage and to a vacuum source.

8 Claims, 2 Drawing Sheets

BIOAEROSOL SLIT IMPACTION SAMPLING DEVICE

CROSS-REFERENCE TO RELATED APPLICATIONS

The present application claims priority from applicant's co-pending provisional application, Ser. No. 60/163,872, filed Nov. 5, 1999 and entitled "Slit-Air Sampler."

TECHNICAL FIELD

The present invention relates generally to a method and apparatus for collecting airborne particles, and more specifically to a slit impaction air sampler that allows for more precise analysis of collected airborne particles.

BACKGROUND OF THE INVENTION

Obtaining accurate samples of airborne particles such as mold spores, pollen, skin fragments, insect parts, various fibers, and other aeroallergens is necessary or desirable for a number of different purposes, including reliable contamination studies. For example, environmental professionals need accurate samples to determine the presence and quality of deleterious such as asbestos fibers in the air. Furthermore, aero-biologists and allergists need accurate samples to identify and quantify airborne pollen and mold spore concentrations for patient diagnosis. Moreover, epidemiologists require accurate samples to determine the presence of particles carrying bacteria, such as that responsible for Legionnaire's Disease, in air-conditioning systems and the like.

Various sampling methods and techniques are well known for use in providing particle analysis in a variety of different areas and applications. One such sampling method is filter sampling, which is well known for use in particle and fiber analysis. With filter sampling methods, air is drawn through a microporous filter as is known and the filter can then be examined under a microscope to determine the type and concentration of particles trapped on the filter. While effective for some purposes, filter sampling is time consuming and provides only limited reliability. For example, large particles such as pollen, often do not remain attached to the filter, separating therefrom during transportation and handling.

Slit or impaction samplers, which direct air at relatively high velocity through a narrow rectangular slit against a tacky material have a number of advantages over filter sampling. With slit air samplers, samples sufficient for analysis can be obtained in minutes rather than hours, the area to be examined is much smaller than the areas provided with filters, and the tacky nature of the material used to collect the sample will retain large particles better than filters. However, the configuration of these designs does not always ensure the desired accurate particle accumulation. Moreover, these samplers typically can only be used in an upright or fixed position and cannot be easily used in confined or restricted spaces because of their relatively large size.

One current sampler, which is described in U.S. Pat. No. 5,693,895, attempts to solve some of these problems by providing a smaller system with a removable sampling cell that minimizes handling of the slide at the sampling site. This sampler, however, requires the usage of a new sampling cell for each sampling run, thereby making it relatively expensive. Additionally, the disclosed sampler suffers from some disadvantages in airflow into the sampler that can lead to an incomplete gathering of air particles and therefore affect any conclusions drawn from an analysis thereof.

SUMMARY OF THE INVENTION

It is therefore an object of the present invention to provide a slit impaction sampling device that allows for the complete collection of a variety of airborne particulates for subsequent analysis.

It is a further object of the present invention to provide a slit impaction sampling device that creates a laminar flow for a more defined impaction trace, which allows for a more precise analysis.

It is still another object of the present invention to provide a slit impaction sampling device that allows for inline calibration during operation to account for pressure drops.

It is yet another object of the present invention to provide a slit impaction sampling device that is reusable.

In accordance with the above and the other objects of the present invention, a slit impaction sampling device is provided. The sampler includes a base with a microscope slide disposed thereon. The microscopic slide has an adhesive media located thereon to assist in adhering airborne particles on the microscopic slide. The base has a top cap secured thereto. The top cap has an inlet opening formed therethrough. The inlet opening has an outer venturi section and an inner laminar section that directs the air flow through the inlet opening into contact with the adhesive media such that the airborne particles form an impaction trace thereon. The air then flows around the microscope slide into an outlet passage and to a vacuum source.

These and other features of the present invention will become apparent from the following description of the invention, when reviewed in accordance with the accompanying drawings and appended claims.

BRIEF DESCRIPTION OF THE DRAWINGS

FIG. 1 is an exploded view of a slit impaction sampling device in accordance with a preferred embodiment of the present invention;

FIG. 2 is an exploded cross-sectional illustration of a slit impaction sampling device in accordance with a preferred embodiment of the present invention;

FIG. 3 is a cross-sectional view of a slit impaction sampling device in an assembled state in accordance with a preferred embodiment of the present invention; and FIG. 4 is a schematic diagram illustrating the air flow during operation of a slit impaction sampling device in accordance with a preferred embodiment of the present invention.

DETAILED DESCRIPTION OF THE PREFERRED EMBODIMENT

Referring now to the figures which illustrate a slit impaction sampling device 10 in accordance with the present invention. The sampling device 10 is suitable for the collection of airborne particles, such as mold spores, pollen, skin fragments, insect parts, various fibers, and other aeroallergens for reliable contamination studies and other analysis. The disclosed sampling device 10 may, however, be used for a variety of purposes, in a variety of locations, and for a variety of different applications. The terms "top," "bottom," "upper," and "lower" and other directional terms are used herein to describe the sampling device 10 with respect to the drawings. These terms are not to be construed as limiting the invention to the orientations shown and described. Further, the term slit impaction device or sampler, refers to a device that allows incoming air to be impacted upon a surface leaving a narrow and recognizable impaction trace which can then be removed for analysis.

Figure 1:
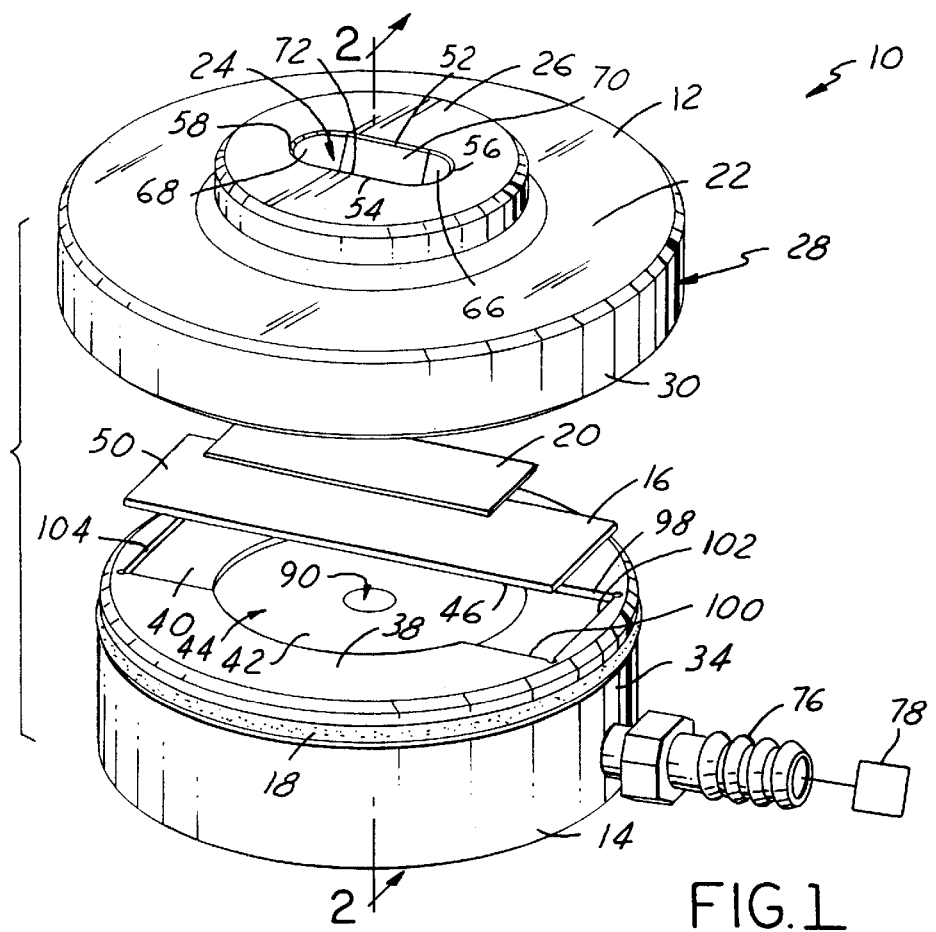
Figure 2:
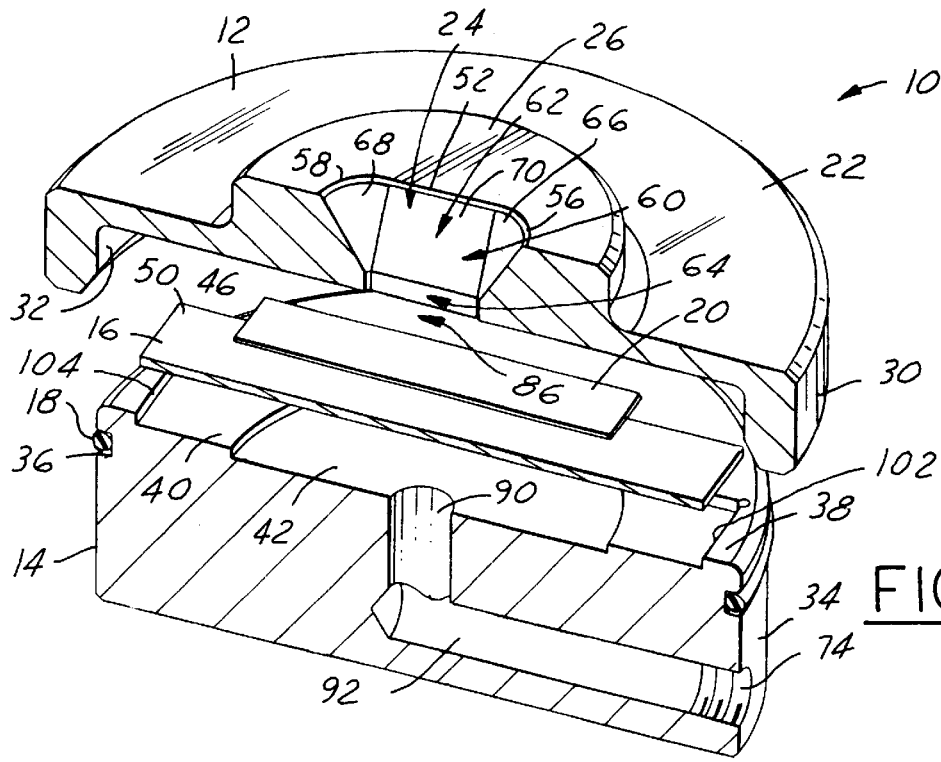

As shown best in FIG. 1, the sampling device 10 includes a top cap 12, a base 14, a microscope slide 16, an o-ring 18, and an adhesive media 20. The sampling device 10 preferably utilizes industry standard slit impaction sampling techniques, as are well known. The sampling device 10 is preferably made of a two-piece aluminum construction and can be assembled and disassembled as needed. Because of the aluminum construction, the device 10 is resistant to most chemicals and environments, and is durable so as to withstand daily use. Alternatively, the device 10 may be constructed of a variety of other materials. The sampling device 10 is preferably relatively small in size to allow placement in smaller places such as HVAC ducts, confined locations, and small corners. However, the device 10 can be constructed in a variety of different sizes.

As shown, the top cap 12 is preferably generally cylindrical in shape and has a top surface 22 with an inlet opening 24 formed therethrough. The inlet opening 24 is preferably formed in a ridge 26 which is raised with respect to the top surface 22. The ridge 26 is also preferably cylindrical in shape and is integrally formed with the top cap 12. The top cap 12 preferably has a flange 28 that extends downwardly and generally perpendicular from the top surface 22. The flange 28 has an outer surface 30 and an inner surface 32. The diameter of the inner surface 32 is preferably sized so it is larger than the diameter of the outer surface 34 of the base 14. The outer surface 30 of the cap 12 is preferably knurled to provide a rough surface for gripping by an operator during assembly and disassembly of the sampling device 10.

Figure 3:
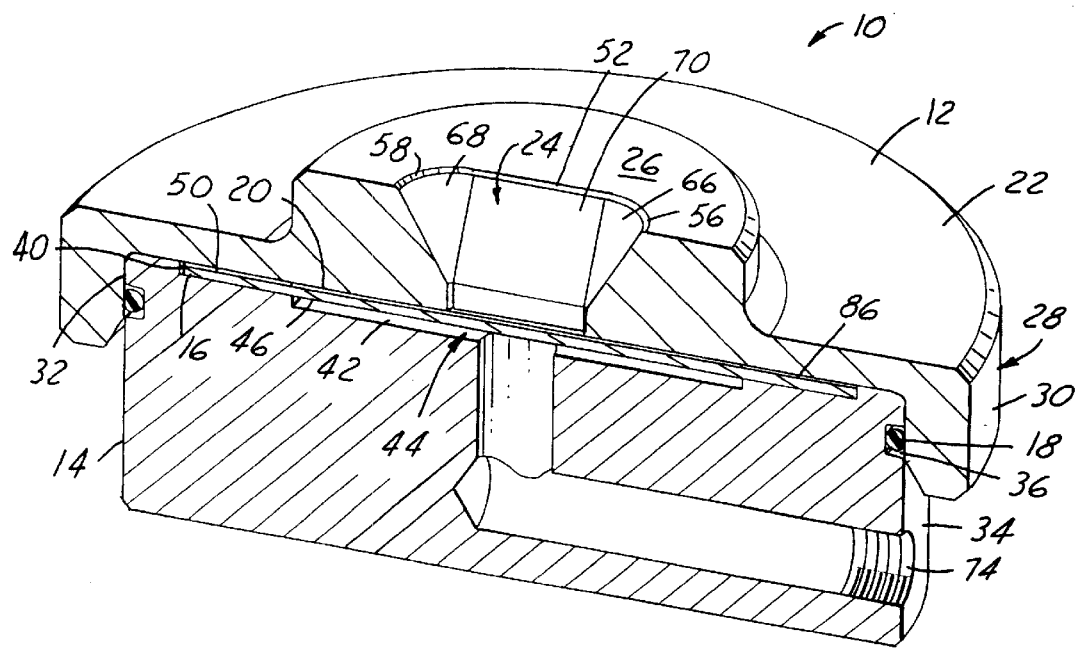

The base 14 preferably has annular groove 36 formed in its outer surface 34. The annular groove 36 is sized to receive the o-ring therein. When the sampling device 10 is assembled (FIG. 3), the flange 28 fits over the outer surface 34 of the base 14 with the o-ring acting to seal and to prevent external air from flowing into the device. The sealing of the device 10 from external air prevents any cross-contamination of the sample along with any bypassing of the inlet opening 24. It should be understood that alternative attachment configurations between the top cap 12 and the base 14 may be utilized, including a threaded connection.

The base 14 has a top surface 38 with a recess 40 formed therein. The recess 40 is approximately sized to receive the microscope slide 16 snugly therein. The recess 40 is generally rectangular in shape with a pair of opposing sides surfaces 98; 100 each connected at right angles by a pair of end surfaces 102, 104. The recess 40 is used to trap the microscope slide 16 to prevent movement during sampling. The top surface 38 of the base 14 has a depression 42 formed therein, which has a greater depth than the depth of the recess 40. The depression 42 is generally circular in shape and extends beyond the boundaries of the slide 16 and allows air to be drawn around the microscope slide 16 through the inlet passageway 62. This configuration leaves a gap 44 between the bottom surface 46 of the microscope slide 16 and the depression, when the microscope slide 16 is located in the recess 40. The recess 40 is preferably sized to accommodate standard 25 mm×75 mm glass microscope slides. Because the microscope slide 16 is not permanently secured in the recess 40, it can be easily removed and placed in an appropriate storage device after a sample has been obtained and then replaced with a new slide. The described sampling device 10 is thus reusable which helps reduce sampling costs.

In accordance with the present invention, a new or fresh microscope slide 16 is handled and/or used each time a sample is obtained. This allows for a visual inspection before each sample is taken to insure that the slide 16 is not broken or damaged prior to its insertion in the device 10. As discussed briefly above, each slide 16 has an adhesive media 20 coated on its upper surface 50. The adhesive is applied just prior to installation of the slide 16 in the recess 40 to insure fresh sampling media 20, which eliminates problems due to expired or dried out adhesive. The adhesive media 20 is preferably located on the middle two-thirds of the slide 16. A variety of adhesive media can be used, including a silicen/hexane alcohol blend or a pure Vaseline. The adhesive is preferably applied by adding two to three small drops to the slide and then spread to cover the appropriate area though the use of an application rod or the like. The coating is then preferably smoothed out in order to provide the most consistent results. The adhesive media 20 provides a tacky surface upon which contaminants in the air can be impacted. While the adhesive media 20 preferably covers the middle two-thirds of the slide 16, it should be understood that the adhesive media 20 can be used to cover all or any portion of the slide 16.

The inlet opening 24 formed in the ridge 26 of the top cap 12 is preferably configured to accelerate air and any air contaminates to an impact velocity onto the adhesive media 20 disposed on the upper surface 50 of the microscope slide 16. The inlet opening 24 is generally oval in shape and has a pair of opposing side portions 52, 54 which are connected at their ends by a respective curved arcuate portion 56, 58. The inlet opening 24 opens to an inlet passageway 60 that extends from the top of the ridge 26 to above the microscope slide 16. The inlet passageway 60 preferably consists of two sections, a tapered or venturi section 62 and a straight or laminar portion (64. The tapered section 62 extends generally downwardly from and narrows with respect to the inlet opening 24 and has a pair of oval end portions 66, 68 that also extend downward and generally inward with respect to a respective one of the curved arcuate portions 56, 58. A pair of converging side portions 70, 72 also extend generally downward from a respective one of the opposing side portions 52, 54 towards the center of the device 10. The converging side portions 70, 72 extend between and connect the oval end portions 66, 68.

The tapered section 62 helps direct inlet air flow towards the straight section 64, as is discussed in more detail below, to create an impaction trace in the adhesive media 20 on the microscope slide 16. The venturi design creates a laminar flow for a more defined impaction trace which allows for more precise analysis.

In order to perform sampling, the outlet 74 of the sampling device 10 is connected to an industry standard high vacuum pump 78 via polyvinyl tubing or the like. The outlet 74 of the sampling device 10 is preferably equipped with a barbed tube fitting 76 or the like, which securely holds the vacuum line in place. As all known impaction samplers have a pressure drop across them, it is essential that the vacuum level be determined and documented. The disclosed sampling device preferably allows for in-line calibration of the vacuum level without jeopardizing the sample. This calibration is accomplished by placing a blank slide 16 in the device 10 and performing the calibration process. For most applications, a vacuum setting of 15 Lpm and a duration of 10 minutes is sufficient for obtaining most samples. After a sample has been obtained, the device 10 can be disassembled, the microscope slide 16 removed and the device 10 cleaned to prevent cross-contamination between samples.

In operation, a clean sampling device 10 is loaded with a standard microscope slide 16, which slide has been prepared with an adhesive media 20 on the middle two-thirds of the slide 16, as discussed above. The media 20 may be applied to the slide 16 before or after it has been inserted into the device 10. The sampling device 10 is then assembled and connected to a precalibrated vacuum source 78 and the device 10 is then placed in the area of interest. The device 10 is then run for approximately 8 to 10 minutes depending upon the environment.

Figure 4:
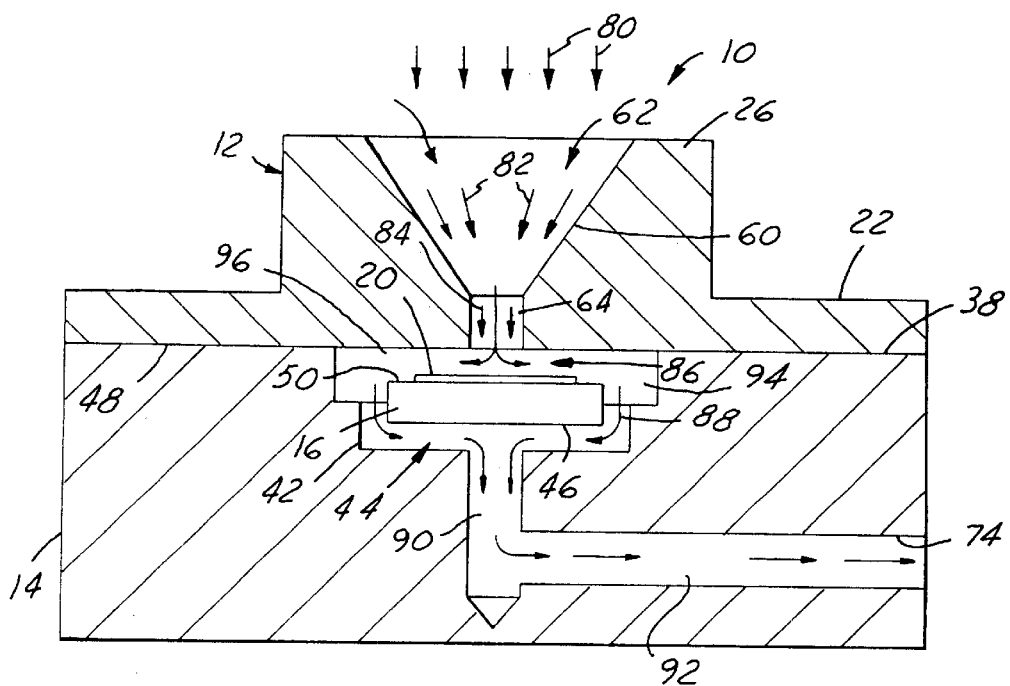

As shown best in FIG. 4, when the vacuum source 78 is turned on, air inlet flow, generally represented by reference number 80, enters the inlet opening 24. The air inlet flow 80 is accelerated due to the tapered section 62, as generally represented by the arrows designated 82. The air flow then enters the straight laminar section 64 which causes the air flow to be directed in a generally perpendicular direction, as indicated by the arrows designated 84. The straight laminar section 64 causes particulates in the air to impact the adhesive media 20 and the microscope slide 16 in a direction perpendicular thereto. This laminar flow, as generally indicated by reference number 84, ensures that all contaminants are directed to the impaction surface. This allows a more defined impaction trace to be obtained by eliminating blow by.

The device 10 includes a space 86 formed between the bottom surface 46 of the top cap 12 and the top of the adhesive media 20. The space 86 generates flow through the sampler and sets up the impaction force of the contaminants. The size of the space 86 is selected to prevent smaller particles from exiting on the sides 94, 96 without striking the adhesive media 20. The height of the space 86 is determined by the depth of the recess 40 in the base 14. As air passes through this space 86, momentum and particle inertia cause the airborne contaminants to impact on the adhesive media 20. Thereafter, the air flows around the microscope slide 16, as generally indicated by the arrows designated 88. The air flow then enters an exist passage 90 before flowing into a vacuum line 92 and through the outlet 74 to the vacuum source 78. The exit passage 90 is located in the center of the circular depression 42 and is cross drilled to the vacuum line 92.

Having now fully described the invention, it will be apparent to one of ordinary skill in the art that many changes and modifications can be made thereto without departing from the spirit or scope of the invention as set forth herein.

What is claimed is:

1. A slit impaction air sampling device, comprising:
    a base portion having a recess formed in a top surface of said base portion, said recess being sized to receive a microscope slide;
    a microscope slide disposed in said recess;
    a depression formed in said top surface of said base portion, said depression having a depth that is larger than a depth of said recess, said depression being sized to allow air flow around said microscope slide;
    an outlet passage in communication with said depression at one end and a vacuum source at another end;
    a top cap secured to said base; and
    a venturi inlet formed in said top cap.

2. The device of claim 1, further comprising an adhesive media applied to said slide.

3. The device of claim 2, wherein said adhesive media is applied to a middle two-thirds portion of said microscope slide.

4. The device of claim 1, wherein said venturi inlet includes a venturi portion and a laminar portion, with said laminar portion being located adjacent said microscope slide.

5. The device of claim 4, wherein said tapered portion includes a pair of opposing converging slide surfaces that are connected by a respective arcuate portion.

6. The device of claim 5, wherein said laminar portion includes a pair of generally planar opposing side surfaces that extend from a respective one of said converging side surfaces.

7. The device of claim 5, wherein said top cap telescopically fits over said base.

8. The device of claim 1, wherein said base has a groove formed in an outer surface for receipt of an o-ring therein to prevent air from leaking into the device when said top cap is secured to said base portion.

* * * * *